(12) United States Patent
Bahatt et al.

(10) Patent No.: US 6,797,139 B2
(45) Date of Patent: Sep. 28, 2004

(54) DETECTION CELL FOR GUIDING EXCITATION LIGHT THEREIN AND METHOD FOR USING SAME

(75) Inventors: Dar Bahatt, Foster City, CA (US); Richard T. Reel, Hayward, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/812,750

(22) Filed: Mar. 19, 2001

(65) Prior Publication Data

US 2002/0131041 A1 Sep. 19, 2002

(51) Int. Cl.$^7$ .............................................. B01D 57/02
(52) U.S. Cl. ...................... 204/452; 204/450; 204/650; 204/400
(58) Field of Search ................................ 204/452, 400, 204/600, 650, 450

(56) References Cited

U.S. PATENT DOCUMENTS

| 4,377,751 A | * | 3/1983 | Kronenberg et al. ...... 250/474.1 |
| 4,675,095 A | | 6/1987 | Kambara et al. |
| 4,997,537 A | * | 3/1991 | Karger et al. ............... 204/453 |

(List continued on next page.)

FOREIGN PATENT DOCUMENTS

| EP | 0 321 736 B1 | 1/1994 |
| WO | WO 93/17325 | 2/1993 |

OTHER PUBLICATIONS

Polson et al., 1999, "Electrophoretic Focusing Preconcentration Technique Using a Continous Buffer System for Capillary Electrophoresis," *J. Microcolumn Separations, 21(2) 98–106*.
Douthart et al., 1996, "Ribbon Channel Plate Rotating Drum DNA Sequencing Device" *Electrophoresis 17, 49–54.*
McCormick et al., 1997 "Microchannel Electrophoretic Seprations of DNA in Injection –Molded Plastic Substrates" *Anal. Chem. 1997, 69 2626–2630.*
Gooijer et al., 1998 "Detector cell based on plastic liquid–core waveguides suitable for aqueous solutions: one –to–two decades improved detection limits in conventional–size column liquid chromatography with absorption detection" *Journal of Chromatography A, 824 (1998)1–5.*
Waterbury et al., 1997, "Long pathlength absorbance spectroscopy: trace analysis of Fe(II) using a 4.5 m liquid core waveguide"*Analytica Chimica Acta 357 (1997) 99–102.*
Alentiev et al., 1996 "High transport parameters and free volume of perfluorodioxole copolymers" *Journal of Membrane Science 126 (1997)123–132.*
Pinnau et al., 1995 " Gas and vapor transport properties of amorphous perfluorinated copolymer membranes based on 2,2–bistrifluoromethyl–4,5–difluoro–1,3–dixole/tetrafluor-roethynlene" *Journal of Membrane Science 109 (1996)125–133.*

*Primary Examiner*—Mark L. Bell
*Assistant Examiner*—Jennine Brown (57) ABSTRACT

The present invention provides a detection cell that comprises a body having a first end that defines a first opening, a second end that defines a second opening, and an internal surface that defines an interior cavity that fluidly connects the first opening and the second opening; wherein the interior cavity is capable of holding a support matrix for receiving a chemical species through the first opening, passing the chemical species through the interior cavity, and discharging the chemical species through the second opening; and wherein at least two portions of the body are capable of providing a first and a second guiding region each having an index of refraction less than that of the support matrix. A system utilizing the detection cell of the present invention is also provided. In another embodiment, the present invention provides a method for guiding light through a support matrix through which a chemical species is passing.

48 Claims, 6 Drawing Sheets

U.S. PATENT DOCUMENTS

| | | |
|---|---|---|
| 5,126,021 A | 6/1992 | Grossman |
| 5,184,192 A | 2/1993 | Gilby et al. |
| 5,268,080 A | 12/1993 | Kambara et al. |
| 5,277,780 A | 1/1994 | Kambara |
| 5,312,535 A * | 5/1994 | Waska et al. ............... 204/603 |
| 5,374,527 A | 12/1994 | Grossman |
| 5,407,638 A * | 4/1995 | Wang ..................... 422/82.09 |
| 5,412,750 A | 5/1995 | Neth |
| 5,414,508 A | 5/1995 | Takahashi et al. |
| 5,416,879 A * | 5/1995 | Liu .......................... 385/125 |
| 5,439,578 A | 8/1995 | Dovichi et al. |
| 5,444,807 A | 8/1995 | Liu |
| 5,516,409 A | 5/1996 | Kambara |
| 5,529,679 A | 6/1996 | Takahashi et al. |
| 5,546,493 A | 8/1996 | Noguchi et al. |
| 5,567,292 A | 10/1996 | Madabhushi et al. |
| 5,570,447 A * | 10/1996 | Liu .......................... 385/125 |
| 5,572,328 A * | 11/1996 | Fouckhardt et al. ........ 356/440 |
| 5,584,982 A | 12/1996 | Dovichi et al. |
| 5,608,517 A | 3/1997 | Munk |
| 5,667,656 A | 9/1997 | Kambara |
| 5,803,575 A | 9/1998 | Ansems et al. |
| 5,815,258 A | 9/1998 | Nakanishi |
| 5,833,826 A | 11/1998 | Nordman |
| 5,833,827 A * | 11/1998 | Anazawa et al. ........... 204/452 |
| 5,857,052 A | 1/1999 | Nath |
| 5,858,187 A | 1/1999 | Ramsey et al. |
| 5,900,934 A * | 5/1999 | Gilby et al. |
| 5,964,998 A * | 10/1999 | Kambara .................... 204/452 |
| 5,991,081 A * | 11/1999 | Haaland et al. ............. 359/580 |
| 6,017,765 A | 1/2000 | Yamada et al. |
| 6,020,207 A | 2/2000 | Liu |
| 6,068,751 A * | 5/2000 | Neukermans ............... 137/606 |
| 6,143,152 A * | 11/2000 | Simpson et al. ............ 204/451 |
| 6,162,341 A | 12/2000 | Nordman et al. |
| 6,188,813 B1 * | 2/2001 | Dourdeville et al. ... 250/227.11 |

* cited by examiner

DETECTION CELL FOR GUIDING EXCITATION LIGHT THEREIN AND METHOD FOR USING SAME

BACKGROUND OF THE INVENTION

1. Field of the Invention

The invention relates generally to a detection cell for receiving a sample to be analyzed photometrically. More specifically, the invention is directed to a detection cell for receiving a sample to be analyzed photometrically that guides excitation light used to detect separated components or peaks through the detection cell, thereby reducing the signal variation of the excitation light and minimizing its potential to wander off axis.

2. Description of Related Art

In biotechnology, separation and analysis of biochemical samples is critically important. Moreover, it is desirable to conduct multiple separations and analyses of the separated components simultaneously to increase the speed and efficiency at which biological samples are evaluated. For example, separation technologies such as electrophoresis are used in DNA sequencing, protein molecular weight determination, genetic mapping, and other types of processes used to gather large amounts of analytical information about particular biological samples. More recently plastic microchips or lab-on-a chip technology is being used to perform separations of biological samples.

Capillary electrophoresis is a particularly preferred separation method. In this method, a sample is electrophoretically separated into its various components or peaks in a capillary tube filled with a buffer solution or gel. This technique allows the use of high electric fields, since the capillary tube efficiently dissipates the resulting heat produced by the electric field. As such, the separations achieved are much better than more traditional electrophoretic systems. In addition, multiple capillary tubes may be closely spaced together and used simultaneously to increase sample through-put.

Analysis or detection of the separated components can be performed while the sample is still located within the capillary and may be accomplished using photometric techniques such as adsorbance and fluorescence, wherein excitation light is directed toward the capillary tube, and light emitted from the sample (e.g., fluorescence) is measured by a detector, thereby providing information about the separated components. Other analytical techniques such as radioactivity detection, electrochemical methods, and mass spectrometry, may also be used to analysis the separated components. Typically, a photometric method such as laser-induced-fluorescence is used wherein the source of the excitation light is a laser that is directed towards the capillary, and the resulting fluorescence from the separated components is measured by a detector. However, the quality of this photometric scheme is reduced due to scattering (e.g., reflection or refraction) of the light by the capillary walls. In systems employing multiple capillary tubes, the laser beam may sequentially scan each capillary tube or may simultaneously traverse the entire plurality of tubes. In either case, light scattering remains a problem, particularly since reflected or refracted light from one capillary tube may interfere with the detection of fluorescence from an adjacent capillary tube or create a complete or significant loss of signal altogether.

As such, there is a need for an improved detection cell that provides better control over the direction within the detection cell of the excitation light that is used to analyze or detect separated components or peaks that have been produced using such techniques such as capillary electrophoresis or microchip technology. Further, there is a need for an improved method for utilizing a detection cell to provide such control over the direction of the excitation light within the detection cell.

SUMMARY OF THE INVENTION

The detection cell of the present invention provides a device for use in analyzing or detecting separated components or peaks from a capillary electrophoresis system, microchip system, or other analytical technique for separating a chemical or biological sample into components. Specifically, the detection cell of the present invention can be used in conjunction with laser-induced fluorescence detection techniques conducted outside of a capillary or microchip channel. The detection cell of the present invention can be used with or without sheath-flow technology and also in conjunction with electro-flow techniques, such as those described in U.S. Pat. No. 5,833,826, incorporated herein by reference.

Specifically, the detection cell of the present invention guides excitation light through the detection cell, which may contain a support matrix comprising a buffer solution or polymer solution, thereby reducing or eliminating the potential for the light to wander off axis. As a result, refraction of the excitation light is reduced or avoided, and thus a stronger signal may be emitted from the separated components making detection of that signal easier. In addition, the excitation light can be confined within the detection cell to that region in which the separated components are flowing, thereby reducing or avoiding a potential loss of signal that may otherwise result if the excitation light wandered off axis and did not illuminate a separated component. Additionally, the present invention provides for easier alignment of the excitation light with the detection cell Furthermore, where the detection cell is made from a low index of refraction material, the background fluorescence is reduced, thereby making detection easier and making the measurement of the resulting fluorescence more robust.

Accordingly, in one embodiment, the present invention provides a detection cell that comprises a body having a first end that defines a first opening, a second end that defines a second opening, and an internal surface that defines an interior cavity that fluidly connects the first opening and the second opening; wherein the interior cavity is capable of holding a support matrix for receiving a chemical species through the first opening, passing the chemical species through the interior cavity, and discharging the chemical species through the second opening; and wherein at least two portions of the body are capable of providing a first and a second guiding region each having an index of refraction less than that of the support matrix.

In another embodiment, the present invention provides a method for guiding light through a support matrix through which a chemical species is passing, comprising directing a beam of light toward a support matrix; and establishing a first and a second guiding region adjacent to and extending along at least a portion of the axis of travel of the beam of light within said support matrix, wherein the first and the second guiding regions each have an index of refraction that is less than that of the support matrix and wherein the first guiding region is approximately opposite the second guiding region, thereby maintaining the beam of light substantially between the first and the second guiding regions.

In yet another embodiment, the present invention provides a system for guiding light through a support matrix to detect a chemical species, comprising a detection cell comprising a body having a first end that defines a first opening, a second end that defines a second opening, and an internal surface that defines an interior cavity that fluidly connects the first opening and the second opening; a support matrix capable of receiving a chemical species through the first opening, passing the chemical species through the interior cavity, and discharging the chemical species through the second opening; wherein at least two portions of the body are capable of providing a first and a second guiding region each having an index of refraction less than that of the support matrix.

These and other features of the invention will appear from the following description from which the preferred embodiments are set forth in detail in conjunction with the accompanying drawings.

DETAILED DESCRIPTION OF THE PREFERRED EMBODIMENTS

The structure and function of the preferred embodiments of the detection cell of the present invention can best be understood by reference to the drawings. Where the same reference designations appear in multiple locations in the drawings, the numerals refer to the same or corresponding structure in those locations.

Figure 1:
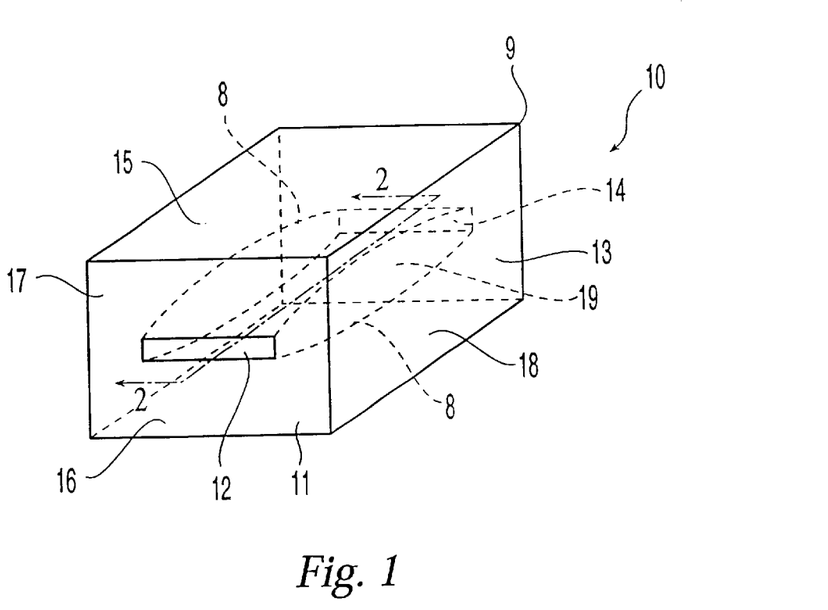
FIG. 1 is a perspective view of a detection cell according to one embodiment of the present invention.

FIG. 1 is a perspective view of a detection cell 10 according to one embodiment of the present invention. The detection cell 10 comprises a body 9 having a first end 11 that defines a first opening 12 for connection to a separation device (not shown) and a second end 13, that defines a second opening 14 for connection to a discharge line or waste receptacle (not shown). The body 9 further comprises a top body portion 15, a bottom body portion 16, and two side body portions 17, 18.

The body 9 also has an internal surface 8 that defines a interior cavity 19. The internal surface 8 surrounds the interior cavity 19. The internal surface is provided by the top body portion 15, the bottom body portion 16, and the two side body portions 17, 18. The interior cavity 19 extends through the detection cell 10 from the first opening 12 at the first end 11 to the second opening 14 at the second end 13. In this manner, the first opening 12 is fluidly connected to the second opening 14, which allows a chemical species to pass through the detection cell 10. It should be appreciated that "chemical species" is used to refer broadly to the passage of any chemical through the detection cell. For example, the chemical species may be a separated component from a chemical separation technique such as electrophoresis, capillary electrophoresis, chromatography or a chemical species received from a channel on a microchip or a slab cell. More specifically, the chemical species may be separated peaks, such as DNA peaks, coming from either a capillary tube or a microchannel on a microchip. It should further be appreciated that the detection cell may be constructed so that the interior cavity is provided by a top body portion and a bottom body portion only and with no side body portions. In this embodiment, the top and bottom body portions would simply meet at their edges to provide the interior cavity.

Figure 2:
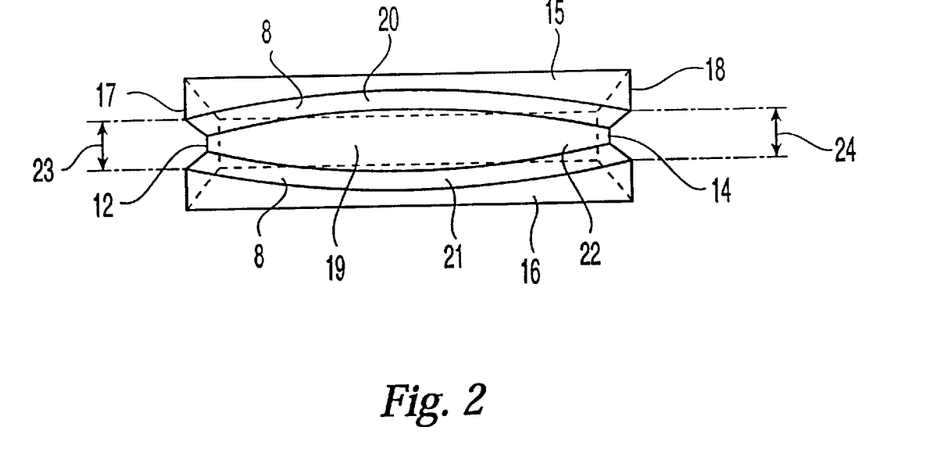
FIG. 2 is a cross-sectional view taken along line 2—2 of FIG. 1.

FIG. 2 is a cross-sectional view taken along line 2—2 of FIG. 1. The internal surface 8 that defines the interior cavity 19 has a top portion 20, a bottom portion 21, and two side portions, only one of which is shown, 22.

The overall dimensions of the detection cell 10 may be varied depending upon its ultimate use. One of skill in the art will appreciate the need to proportion the outer size of the detection cell 10 to accommodate the use of excitation light, for example, a laser, and to accommodate the use of a detector to receive and detect signals from the chemical species passing from the chemical species in the detection cell. The dimensions may also be dependent upon the size of the first and second openings 12, 14 required to mate with a separation device or discharge line, respectively. In addition, the dimensions may be dependent upon the size of the interior cavity 19, which is discussed below. However, a preferred outer dimension for the detection cell is 5–50 mm×5–50 mm×2–20 mm, and a more preferred dimension is 10–50 mm by 10–30 mm by 4–20 mm.

The first opening 12 at the first end 11 may be constructed to be any shape or size necessary to mate to any desired separation device. For example, detection cell 10 may be mated to a plurality of capillary tubes in a capillary electrophoresis device or to the channels or array of channels of a microchip. In either case, one of skill in the art will understand how such a fluid connection or mating may be made. For example, a flat array of capillary tubes may be mated to the first opening 12 using an appropriate connector that fluidly seals against the detection cell. The same is true for connection to the channel outlet of a microchip. In general, one of skill in the art will appreciate that the opening may be constructed or configured to mate a given dimension presented by the separation device. Preferably, however, the first opening 12 is rectangular in shape, and a connector may be fashioned to transition from the separation device to the rectangular opening of the detection cell. Such a connector would preferably make a fluid-tight connection between the separation device and the first opening 12. However, a preferred size for the first opening 12 is 0.2–10 mm×5–50 mm, and a more preferred size is 2–5 mm×10–30 mm. U.S. Pat. No. 6,162,342, incorporated herein by reference, provides additional information regarding this mating.

Similarly, the second opening 14 may be constructed to be any shape or size necessary to mate to a discharge line or waste receptacle. In general, one of skill in the art will appreciate that the opening may be constructed or configured to mate a given dimension presented by the discharge line or waste receptacle. Again, the second opening 14 is preferably rectangular in shape, and a connector may be fashioned to transition from the rectangular opening of the detection cell to a discharge line or waste receptacle. Such a connector would preferably make a fluid-tight connection between the separation device and the second opening 14. However, a preferred size for the second opening 14 is 0.2–10 mm×5–50 mm, and a more preferred size is 2–5 mm×10–30 mm.

The interior cavity 19 may take any shape that allows the passage of chemical species from the first opening 12 to the second opening 14. In a preferred embodiment, the interior cavity 19 is capable of holding a support matrix that extends from the first opening 12 to the second opening 14 that permits the movement or diffusion of a chemical species received from a separation device from the first opening 12 through the support matrix to the second opening 14. One of skill in the art will appreciate the various materials that may be used as a support matrix. For example, the support matrix may comprise a buffer solution such as Na-TAPS or a separation solution such as a polymer comprising linear polyacrylamide. It should be appreciated that the length of the interior cavity 19 that may be used for proper operation maybe dependent upon the specific chemical species moving through the detection cell 10 and the specific support matrix used. As noted above, the dimensions of the interior cavity will be dependent to some extent upon the external dimensions of the detection cell required to mate properly to the separation device that feeds the chemical species to the detection cell, such as a capillary array or planar array, such as a microchip array, and the dimensions necessary to be able to detect signals emitted from the separated chemical species.

In a more preferred embodiment, the interior cavity 19 is shaped so that the vertical distance between the top portion 20 of the internal surface 8 and the bottom portion 21 of the internal surface 8 is greater than the vertical height of the first and second openings 12, 14. As shown in FIG. 2, this may be accomplished by using a concave top portion 20 of internal surface 8 and a concave bottom portion 21 of internal surface 8. It is not necessary that both the top portion 20 and the bottom portion 21 have the same shape or that the shape be necessarily inherently symmetrical. However, in this preferred embodiment, each of these portions 20, 21 has a substantially inherent symmetrical shape, in this case, concave. In addition, this preferred embodiment shows that the symmetrical shape of both of these portions 20, 21 is also symmetrical relative to each other. These same types of symmetry may be utilized with other shapes of interior cavity 19. For example, the interior cavity may be cubicle or cylindrical in shape, wherein the distances between the top and bottom of the interior cavity are still greater than the than the vertical height of the first and second openings.

Figure 2A:
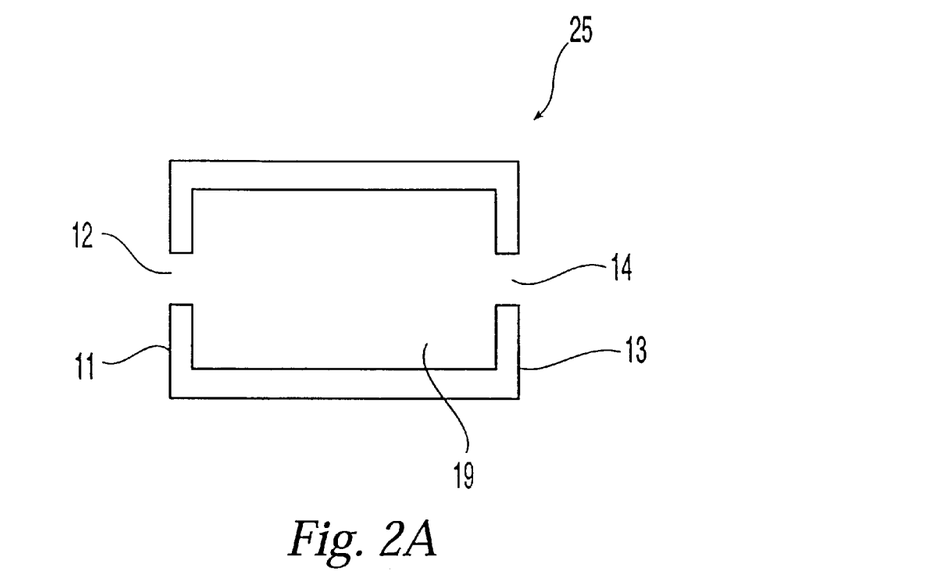
FIG. 2A shows a detection cell according to another embodiment of the present invention.

FIG. 2A shows a detection cell 25 according to another embodiment of the present invention. In this embodiment, the interior cavity 19 may be dimensioned at the first end 11 and the second end 13 to be larger than the first opening 12 or the second opening 14.

Figure 2B:
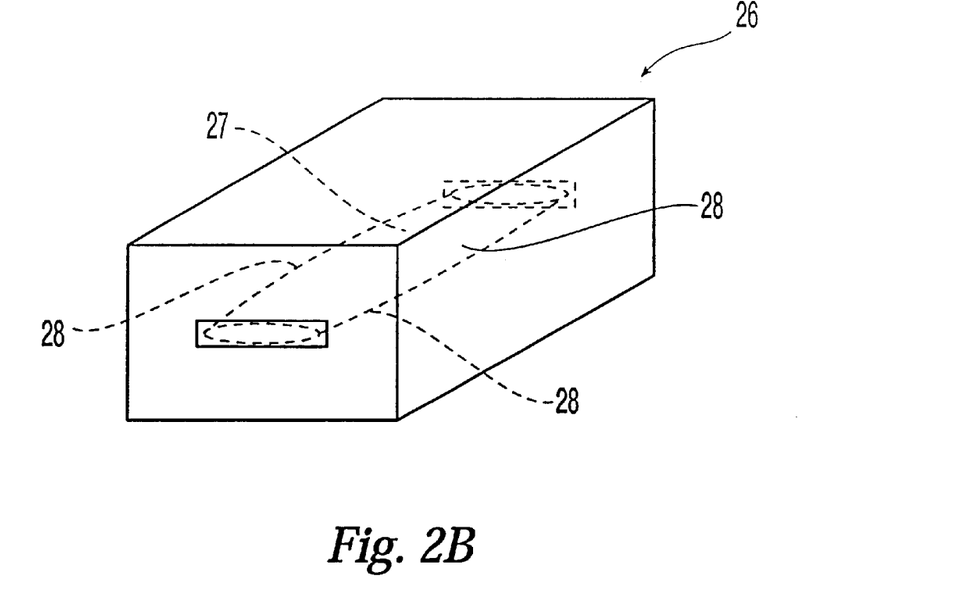
FIG. 2B is a perspective view of a detection cell according to another embodiment of the present invention

FIG. 2B is a perspective view of a detection cell 26 according to another embodiment of the present invention. In this embodiment, the interior cavity 19 is comprised of essentially two mated curved portions, such that there are no sides. Specifically, the top body portion 27 and the bottom body portion 28 may be curved surfaces that simply mate at their respective longitudinal edges 28.

Figure 3:
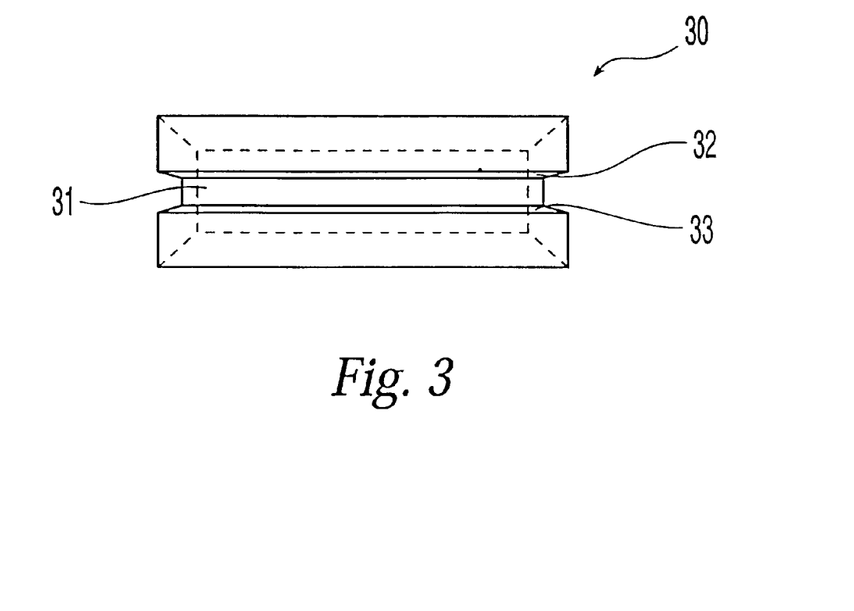
FIG. 3 is a cross-sectional view of a detection cell according to another embodiment of the present invention.

FIG. 3 is a cross-sectional view of a detection cell according to another embodiment of the present invention. FIG. 3 shows a detection cell 30 that is similar to the detection cell 10 shown in FIGS. 1 and 2, except that the shape of the interior cavity 31 is different. In this particular embodiment, both the top portion 32 and the bottom portion 33 of the internal surface are flat. In this embodiment it is preferred to make the distance between the top portion 32 and the bottom portion 33 approximately 10–300 $\mu$m and more preferably 100–300 $\mu$m and even more preferably 100 $\mu$m. One specific embodiment, however, may utilize a distance of 300 $\mu$m.

In operation, the detection cell of the present invention is used to hold a support matrix through which separated chemical species may pass. The separated chemical species are produced from any system used to separate chemical components in a mixture. For example, the detection cell may be connect to the output of a capillary electrophoresis system, microchip system, or other analytical technique for separating a chemical or biological sample into its components.

As these separated chemical species pass through the support matrix of the detection cell, excitation light is directed toward the detection cell to illuminate the separated chemical species, which, depending upon their chemical properties will give off light that can be detected by a detector to assist in identification of that particular separated chemical species. For example, a laser may be used as the source of excitation light, wherein a laser is directed toward the support matrix and upon illuminating certain of the chemical species causing them to fluoresce. This fluorescence is then detected by the detector to identify the separated chemical species.

Generally, the detection cell of the present invention is constructed to guide this excitation light through the detection cell, thereby reducing or eliminating the potential for the light to wander off axis or vary from its intended direction of travel. By guiding the excitation light through the detection cell and support matrix therein, scatter, specifically reflection and refraction, of the excitation light is reduced or avoided. This may provide for more direct contact between the excitation light in the support matrix and the various separated chemical species, since the excitation light has a lower probability of wandering as it travels through the support matrix or leaving the support matrix. This may also provide for emission of a stronger signal from the separated components making detection of that signal easier and may provide a stronger signal relative to the background fluorescence.

The detection cell of the present invention guides the excitation light through the detection cell by the use of guiding regions. Generally, these guiding regions are regions constructed adjacent to, overlapping with, or within the support matrix and have a lower index of refraction than the bulk support matrix through which the excitation light is traveling. As such, the excitation light will tend not to pass through these guiding regions, since the light will naturally be diverted from a lower index of refractive material.

It is preferred to construct these guiding regions so that they are positioned approximately adjacent or along that portion of the intended path that the excitation light will travel through the support matrix to substantially maintain the excitation light along this intended path or axis of travel, thereby reducing the potential for the excitation light to wander from that intended path. More preferably, the guiding regions are oriented to extend along the entire path or axis of travel that the excitation light is intended to take within the support matrix.

It is preferable to construct a pair of guiding regions that extend substantially along the entire path or axis of travel that the excitation light is intended to take within the support matrix and that are on substantially disposed opposite to one another or on opposite sides of the intended axis of travel of the excitation light. As a result the excitation light may be substantially maintained or confined between that pair of guiding regions.

More preferably, multiple guiding regions may be constructed substantially along the entire path or axis of travel that the excitation light is intended to take within the support matrix, thereby substantially surrounding the beam of excitation light as it travels through the support matrix, in essence, creating a conduit through which the excitation light may travel. For example, the excitation light may be essentially bounded on all sides by using two pairs of guiding regions both oriented substantially along the entire path or axis of travel that the excitation light is intended to take within the support matrix, where one pair of guiding regions are disposed substantially on opposite sides of the axis of travel of the excitation light and where the other pair of guiding regions are also disposed substantially on opposite sides of the axis of travel of the excitation light but are also disposed between the first pair of guiding regions. For example, in a more specific embodiment discussed in more detail below, one pair of guiding regions could be configured to be on the top and bottom of the detection cell and the second pair could be configured to be on the sides of the detection cell. In this manner, the excitation light would be substantially confined in two directions: vertical and horizontal. It should be appreciated, however, that any number of guiding regions may be used and their orientation to each other may be constructed as desired.

Figure 4:
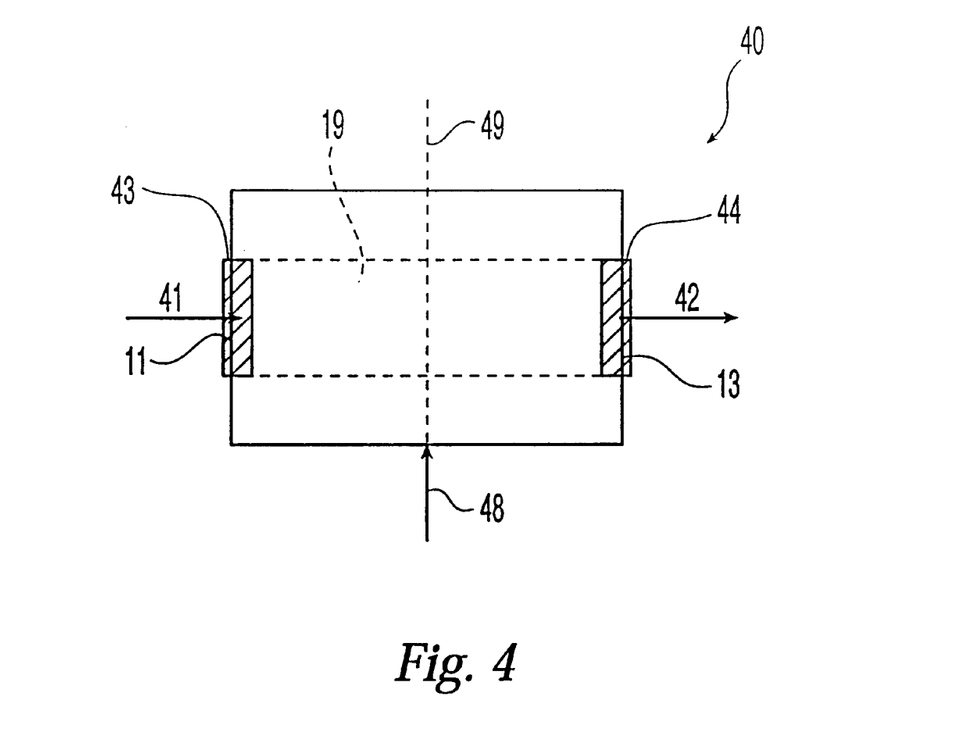
FIG. 4 is a top view of a detection cell according to one embodiment of the present invention.

FIG. 4 is a top view of a detection cell 40 according to one embodiment of the present invention. Separated chemical species 41 enter the detection cell 40 at the first end 11, pass through the interior cavity 19, and exit the detection cell 40 at the second end 13. Excitation light 48 is directed to the detection cell 40 to illuminate the separated chemical species. A pair of guiding regions 43, 44 are established at the first end 11 and the second end 13 to substantially maintain the excitation light between these guiding regions, thereby reducing the scatter of the excitation light in a horizontal direction, relative to the orientation of the detection cell 40 in FIG. 4, as it travels through the support matrix held within the interior cavity 19. As such, guiding regions 43, 44 are established along or beside the axis or direction of travel 49 of the excitation light 48 within the support matrix. More specifically, guiding regions 43, 44 can be established along the first opening (not shown) at the first end 11 and at the second opening (not shown) at the second end 13, respectively. In other words, the guiding regions 43, 44 would extend in a direction parallel to the axis of travel 49 along the entire first opening and second opening, respectively. Therefore, it should be appreciated that guiding regions 43, 44 may be oriented to extend only along the first opening or second opening or along the entire side of the support matrix at the first and second ends 11, 13, in those cases where the first and second openings are smaller than the length of the interior cavity 19 and the support matrix at the first or second ends, such as the detection cell of FIG. 2A.

It should further be appreciated, however, that guiding regions 43, 44 may not necessarily extend along the entire side of the support matrix as shown or along the entire first opening or second opening. These guiding regions 43, 44 may be established simply along a portion of the axis of travel 49 within the support matrix. It should also be appreciated that the representation of the guiding regions 43, 44 in FIG. 4 are to illustrate the approximate location of these guiding regions 43, 44 only and should not be deemed to be limiting as to the actual dimensions of any guiding region. As will be discussed further below, many factors will affect the size or dimensions and strength of the guiding regions.

Figure 5:
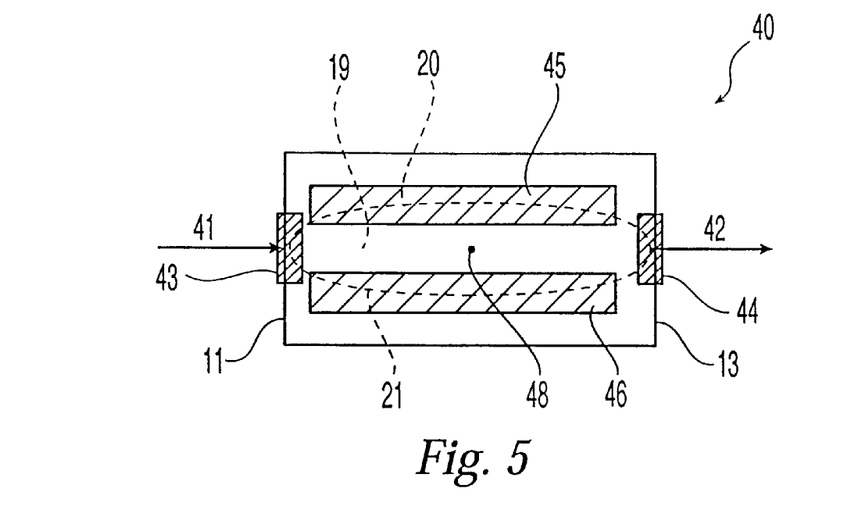
FIG. 5 is a side view of the detection cell of FIG. 4 according to another embodiment of the present invention.

FIG. 5 is a side view of the detection cell of FIG. 4 according to another embodiment of the present invention. In this embodiment, guiding regions 43, 44 are established along the first opening (not shown) at the first end 11 and at the second opening (not shown) at the second end 13, and a second pair of guiding regions 45, 46 are established along the top and bottom portions 20, 21 of the interior cavity 19. It should be appreciated that the excitation light 48 is shown as a point, since its direction or travel or intended path or axis of travel is normal to the page. Guiding regions 45, 46 on the top and bottom of the detection cell complement the guiding regions 43, 44 at the first and second ends 11, 13, by substantially maintaining the excitation light in a vertical direction, relative to the orientation of the detection cell 40 in FIG. 5, as it travels through the support matrix held within the interior cavity 19. As such, conduit through the support matrix within the interior cavity 19 has been established through which the excitation light 48 is essentially forced to travel.

Figure 6:
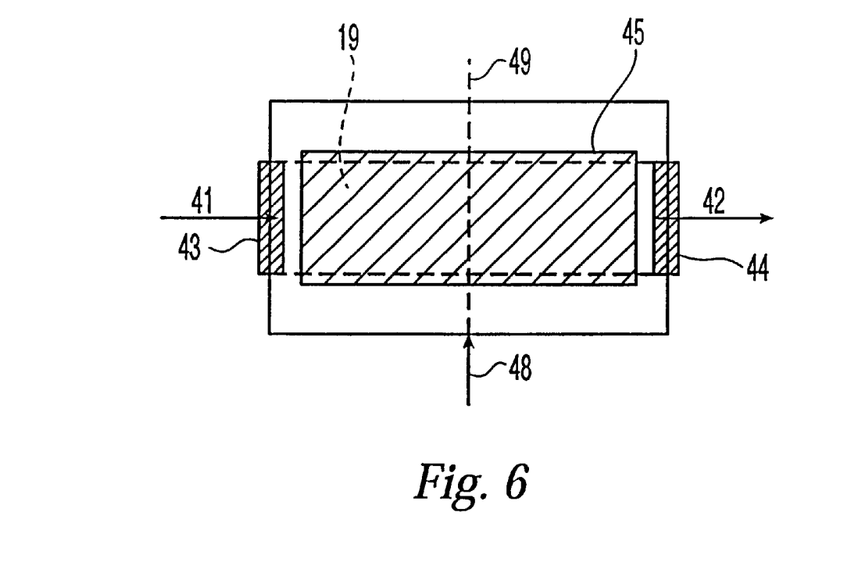
FIG. 6 is a top view of the detection cell of FIG. 4 according to one embodiment of the present invention.

FIG. 6 is top view of the detection cell of FIG. 4 according to the embodiment of FIG. 5. The top guiding region 45 is shown to illustrate that it basically covers the top of the interior cavity 19, so that this guiding region also extends substantially along the intended path or direction of travel of the excitation light 48 within the support matrix. It should be appreciated, in a similar manner to the guiding regions 43, 44 established at the first and second ends, that the top and bottom guiding regions 45, 46 may be any size such that it may not be necessary to cover the entire top and bottom of the interior cavity 19. Again, it should be appreciated that the representation of the guiding regions 45, 46 in FIG. 5 are to illustrate the approximate location of these guiding regions 45, 46 only and should not be deemed to be limiting as to the actual dimensions of any guiding region. As will be discussed further below, many factors will affect the size or dimensions and strength of the guiding regions.

With respect to the establishment of guiding regions, referring back to FIGS. 1 and 2 and the shape of the interior cavity 19, in one embodiment, it is preferable to make the vertical distance between the top portion 20 of the internal surface 8 and the bottom portion 21 of the internal surface 8 greater than the vertical height of the first and second openings 12, 14. More preferably, it is desirable to construct the detection cell 10 such that the distance 23, 24 between the top portion 20 of the internal surface 8 and the opposing bottom portion 21 of the internal surface 8 are close enough such that in operation the application of an electric field across the detection cell would result in a sufficient current density along at least a portion of the first end 11 and separately along at least a portion of the second end 13 to cause an increase in the temperature along these portions of the first opening 12 and the second opening 14. This higher temperature, in turn, may provide an index of refraction in these portions that is lower than the support matrix itself contained within the interior cavity 19. As a result, guiding regions may be established at the first opening 12 and at the second opening 14 in a manner as shown in FIG. 4.

It should be appreciated that these guiding regions may essentially extend along the entire length of the first opening 12 and the second opening 14. As such, these guiding regions are essentially parallel to each other and to the direction of travel of the excitation light through the detection cell 10, thereby providing essentially an conduit or waveguide through which the excitation light may travel. In this particular embodiment and referring to FIG. 2, having guiding regions that extend along the first opening 12 and the second opening 14 essentially reduces or prevents the excitation light from wandering in a left to right direction or horizontal direction.

It should be appreciated that these guiding regions may encompass portions of the support matrix itself, since the temperature may be increased in portions of the support matrix in proximity to the first opening 12 and the second opening 14. As such, comparisons between the index of refraction of the guiding regions and the support matrix refer to the differences between the index of refraction of these guiding regions and the index of refraction of the bulk support matrix.

Figure 7:
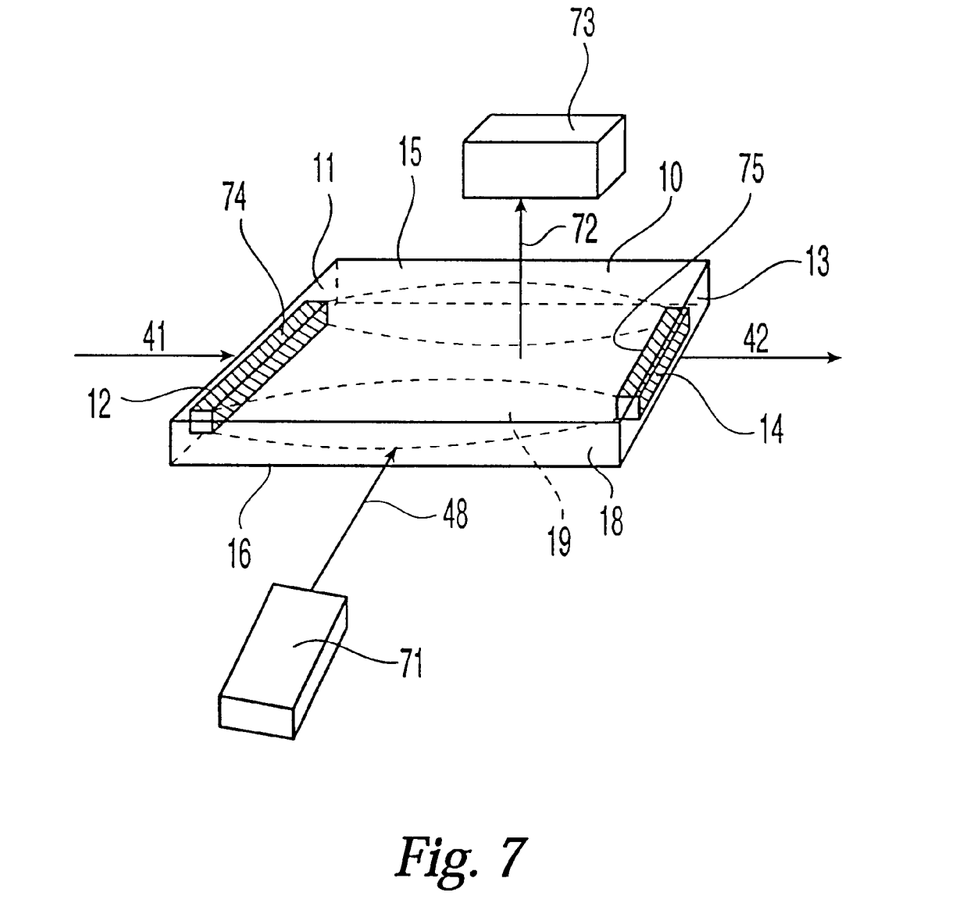
FIG. 7 is a diagrammatic view of a system utilizing a detection cell according to one embodiment of the present invention.

FIG. 7 is a diagrammatic view of a system utilizing a detection cell according to one embodiment of the present invention. FIG. 7 shows the establishment and use of one pair of guiding regions along at least a portion of the first end 11 and the second end 13 by using the application of an electric field as described above. Chemical species 41 enter the detection cell 10 at the first opening 12, pass through the support matrix of the detection cell 10 contained within the interior cavity 19, and the chemical species 42 exit the detection cell 10 at the second opening 14. An excitation light source 71 directs excitation light 48 towards a side body portion 18, preferably in a direction normal to the side body portion 18, substantially perpendicular to the direction of flow of the chemical species 41, and at a height on side body portion 18 such that the excitation light 48 will be directed through interior cavity 19. Light 72 emitted from separated components, for example, fluorescence, within the support matrix contained within the detection cell 10 passes through the top portion of the detection cell and is received by a detector 73 for analysis and processing. It should be appreciated that the orientation of the detector relative to the detection cell may be altered, for example, such that the detector 73 is positioned beneath the detection cell 10 and receives the emitted light 72 from the bottom of the detection cell 10.

As describe above, application of an electric field across the detection cell 10 will establish a first guiding region 74 and a second guiding region 75 along at least a portion of the first end 11 and along at least a portion of the second end 13, respectively, based upon the proximity of the top portion 20 of the internal surface 8 and the bottom portion 21 of the internal surface 8 at the first opening 12 and the second opening 14. These guiding regions preferably extend along at least a portion of the first opening 12 and the second opening 14, and more preferably along the entire first opening 12 and the second opening 14. Generally, these guiding regions 74, 75 are established to substantially maintain or bound the excitation light 48 between them, thereby reducing the potential for the excitation light 48 to wander in a left to right or right to left direction as it travels through the support matrix within the interior cavity 19. More preferably, these guiding regions are substantially parallel to one another and to the direction or axis of travel of the excitation light 48 through the support matrix contained in the interior cavity 19. These guiding regions 74, 75, in turn, act as a conduit or waveguide to confine the excitation light 48 between these regions 74, 75. In essence these guiding regions 74, 75 prevent the excitation light 48 from wandering in a left to right direction in FIG. 7, or, stated differently, from wandering between the first end 11 and the second end 13.

It is preferred that the distances 23, 24 between the opposing top and bottom portions 20, 21 are close enough to cause at least a 0.1° C. temperature difference between the guiding regions 74, 75 and the support matrix upon application of an electric current. As noted previously, it is preferable to cause at least a 0.1° C. temperature difference between the guiding regions 74, 75, wherein the distance between the opposing top and bottom portions 20, 21 is approximately 10–300, $\mu$m and more preferably 100–300, $\mu$m and even more preferably 100 $\mu$m. One specific embodiment, however, may utilize a distance of 300 $\mu$m and a current density of approximately $2.5 \times 10^{-3}$ $\mu$amps/$\mu$m$^2$, which corresponds to approximately 14 milliamps using a capillary array having a pitch of 240 $\mu$m (i.e., the distance from the middle of each capillary tube to the adjacent capillary tube), wherein each capillary tube has an outer diameter of approximately 150 $\mu$m and an inner diameter of approximately 50 $\mu$m. As noted above, it should be appreciated that since the guiding regions may encompass a portion of the support matrix, the temperature difference is deemed to be between the temperature of the guiding region and the temperature of the bulk support matrix.

To provide guiding regions 74, 75, it is even more preferable to construct the detection cell 10 such that the distances 23, 24 are approximately 100 $\mu$m at the first end 11 and at the second end 13. It should be appreciated, however, that the distances between the top portion 20 and the bottom portion 21 may, alternatively, be different at the first end 11 and the second end 16. However, it should be appreciated that an optimal distance between the top portion and the bottom portion is a function of many factors, including the physio-chemical, thermal, and electrical properties, including electrical conductivity, of the support matrix and the voltage or current actually applied to create the electric field.

The application of the electric field may be accomplished by any method known in the art. In a particular embodiment, discussed further in connection with FIG. 8, the electric field used in electrophoresis may supply the necessary current. For example, using an electrode at the front of an electrophoresis system and a second electrode electrically connected to the discharge stream from the detection cell of the present invention and applying a voltage between these two electrodes may supply the requisite current to effect the desired electrical field at the first end 11 and the second end 12. One of skill in the art will appreciate the relationship between the distance between the top and bottom portion of the detection cell, the properties of the support matrix, and the applied current to arrive at optimal performance.

In another embodiment of the present invention the materials of construction used to make the detection cell may be utilized to provide additional guiding regions. Generally, however, the detection cell of the present invention may be constructed of any material consistent with the intended use of the detection cell. Generally, one of skill in the art will appreciate that this material should be chemically compatible with the support matrix and the separated components that may travel through the support matrix. In addition, the optical properties of the material needs to be sufficient to allow the excitation light and emitted light to pass through the structural body of the detection cell. Further, the material should preferably have a relatively low index of refraction, a low background fluorescence signal, be capable of withstanding high pressure operation, and be chemically resistant and inert.

In a preferred embodiment, the entire detection cell is made from a material that has an index of refraction that is lower than the support matrix to be used. Referring back to FIG. 2, by constructing the detection cell out of a material that has a low index of refraction compared to the support matrix, top portion 20 of the internal surface 8 and the opposing bottom portion 21 of the internal surface 8 will have an index of refraction that is lower than that of the support matrix. As a result, these surfaces are also guiding regions, since they may act to confine the excitation light between them. As discussed in connection with FIG. 5, establishing guiding regions 45, 46 at the top and bottom of the interior cavity 19 may reduce the ability of the excitation light 48 from wandering in a vertical direction or, stated differently, between the top body portion 15 and the opposing bottom body portion 16 of FIG. 2. An example of one such material is amorphous fluoropolymer, such as TEFLON-AF, that has an index of refraction of approximately 1.29 to 1.31. One of skill in the art would be able to select other materials that would provide the necessary index of refraction, as well as having the other properties discussed above and as a function of the support matrix itself. It should be appreciated that providing guiding regions at the top and bottom of the interior cavity may be used alone or in conjunction with the provision of guiding regions at the first and second ends as shown in FIG. 7, resulting in the use of multiple guiding regions as shown in connection with FIGS. 5 and 6.

In an alternative embodiment, the detection cell may be made from another material, such as quartz or fused silica, and portions of the internal surface may be coated with a material having a lower index of refraction, such an amorphous fluoropolymer, compared to the support matrix. Again, referring back to FIGS. 2 and 4, the top portion 20 of the internal surface 8 and the opposing bottom portion 21 of the internal surface 8 may be coated with a material that has a refractive index that is lower than that of the support matrix. In this particular embodiment, the coating provides a guiding region. That is, the coating on the top portion 20 and on the bottom portion 21 act to confine the excitation light between them. For example, in connection with FIG. 7, thereby preventing or reducing the potential for the excitation light from wandering in a top to bottom direction in FIG. 4 or, stated differently, between the top body portion 15 and the opposing bottom body portion 16.

It should be appreciated that the guiding regions provided by the use of a material having an index of refraction, either inherently or by using a coating, that is lower than the support matrix may be used in connection with any shape of the interior cavity. As described above, guiding regions were constructed for the embodiment shown in FIGS. 1 and 2 having symmetrically curved top and bottom portions 20, 21 of the internal surface 8. Alternatively, and referring to FIG. 3, guiding regions could be constructed with flat top and bottom portions 32, 33. Further still, these guiding regions may be constructed in the embodiment shown in FIG. 2A or 2B. Preferably, the shape of the interior cavity comprises the shape as shown in connection with FIGS. 1 and 2.

It should be recognized, however, that to provide the guiding regions according to the present invention, it is preferable to have substantially opposing guiding regions so that the excitation light can be confined along its intended path of travel through the support matrix or detection cell. In other words, by only creating one guiding region, for example by using a low index of refraction coating on a top portion of the internal surface and not on the opposing bottom portion, would not maintain the excitation light between those two portions. The excitation light, while it would not wander toward the top portion, it could wander towards the bottom portion. Therefore, to create guiding portions that cooperatively focus or channel the excitation light, it is desirable to utilize opposing guiding regions.

Opposing guiding regions may be provided by utilizing opposing portions of the internal surface. As described above, using a low index of refraction material or coating on the top and opposing bottom portions of the internal surface creates two such opposing guiding regions that keep the excitation light from wandering in a top to bottom direction. With respect to the use of an electric field, the ends of the top and opposing bottom portions are utilized to provide opposing guiding regions. It should be appreciated, however, that the term "opposing" means substantially opposite one another.

It should be appreciated that the guiding regions established by using an appropriate construction of the interior cavity and an electric field or by making the top and bottom portions of the interior surface out of a material having an index of refraction lower than the support matrix, or using a coating on those portions, may be used independently or in combination. In combination, there would be up to four guiding regions that would essentially surround the excitation light. Preferably, two guiding regions would be established along the first end and second end and two guiding regions would be established along the top and bottom of the interior cavity. As such, the combination of these four guiding regions would prevent the excitation light from wandering in both the up-down direction and the left-right direction. This would allow the excitation light to remain more focused as it travels through the support matrix.

In using the guiding regions established using the top and bottom portions of the interior surface but without the electric field, it should be appreciated that an alternative embodiment comprises the use of a mirrored surface. For example, a front surface- or back surface-coated mirror may be used on both the top or bottom portion of the interior surface depending upon the orientation of the detector. If the detector is positioned above the detection cell, such that the excitation light must pass through the top portion of the detection cell, then the mirrored surface would be used on the bottom portion of the detection cell. If the detector is position below the detection cell, such that the excitation light must pass through the bottom portion of the detection cell, then the mirrored surface would be used on the top portion of the detection cell. In addition, it may be possible to combine the use of a mirrored surface on either the top or bottom portion of the detection cell with a low index of refractive material or coating on the opposite interior surface of the detection cell. It should be appreciated that it may be possible, however, to utilize a mirrored surface for the top or bottom portion alone as previously described. It should be appreciated, however, that it is preferable to use a back surface-coated mirrored surface if such is used in combination with the use of an electric field as described above to avoid interference with the electric field that may be created by a front surface-coated mirrored surface.

In actually constructing or manufacturing the detection cell of the present invention, it should be appreciated that the various portions of the body of the detection cell are not necessarily physically separable components. Referring to FIG. 1, for example, the top body portion 15, the bottom body portion 16, and the two side body portions 17, 18 may be integral to one another. In one embodiment, for example, the detection cell 10 may be constructed by mating two halves of the cell, which may comprise a top half and a bottom half or a left half and a right half. As one of skill in the art will appreciate, a detection cell constructed by mating a top half and a bottom half would translate to top body portion 15 being integral to the top halves of the two side body portions 17, 18, and bottom body portion 16 being integral to the bottom halves of the two side body portions 17, 18. Regardless, one of skill in the art will appreciate the numerous ways in which the detection cell of the present invention may be machined or constructed.

Figure 8:
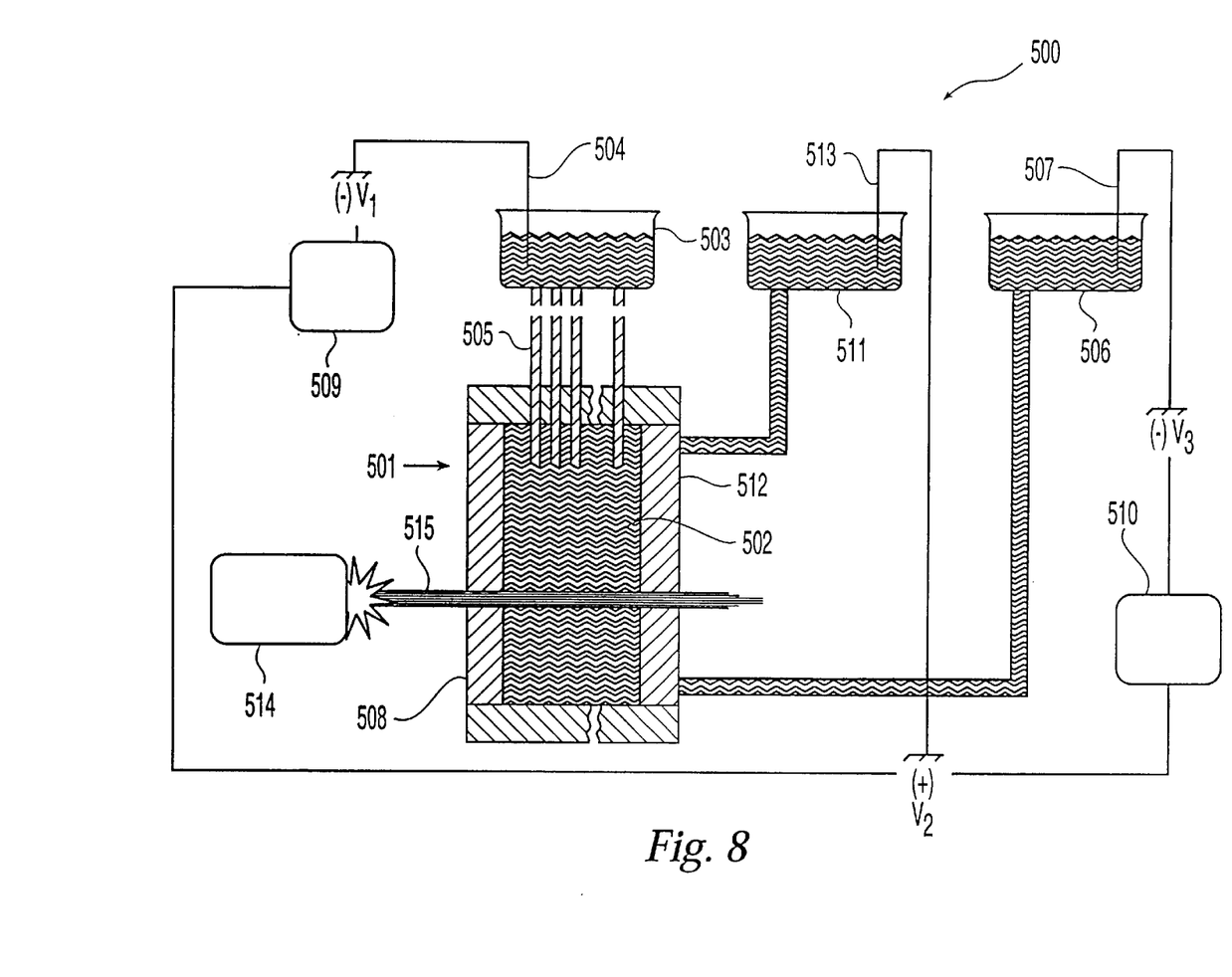
FIG. 8 is a schematic view of a system utilizing a detection cell according to one embodiment of the present invention.

FIG. 8 is a schematic view of a system utilizing a detection cell according to one embodiment of the present invention. Specifically, a detection cell 501 made according to any embodiment of the present invention can be utilized in a system 500 that utilizes technology as described in U.S. Pat. No. 5,883,826, incorporated herein in its entirety, comprising a support matrix 502 contained within the detection cell 501, a first buffer system 503 in fluid contact with the inlet side of a separation device 505, shown here as a plurality of capillary tubes, a second buffer system 506 in fluid contact with the support matrix 502 at a second end 508 of the detection cell 501, a first electrode 504 in electrical contact with the first buffer system 503, a second electrode 507 in electrical contact with the second buffer system 506, a first voltage supply 509 electrically connected to the first electrode 504, a second voltage supply 510 electrically connected to the second electrode 507, a third buffer system 511 in fluid contact with a first end 512 of the detection cell 501, a focusing electrode 513 in electrical contact with the third buffer system 511, an excitation light source 514, and a detector (not shown). It should be appreciated that each buffer system is an electrically conductive solution.

In operation, the first electrode 504 is maintained at a first voltage $V_1$ using the first voltage supply 509 and is in electrical contact with the inlet side of a separation device 505 through the first buffer system 503. The second electrode 507 is maintained at a second voltage $V_2$ also using the first voltage supply 509 and is in electrical contact with the second end 508 of the detection cell 501 through the second buffer system 506. The focusing electrode is maintained at a third voltage $V_3$ using the second voltage supply 510 and is in electrical contact with a first end 512 of the detection cell 501 through the third buffer system 511.

In this embodiment, the separated components eluding from the separation device 505 enter the detection cell at the first end 512. At this first end 512 of the detection cell, the electrical voltage applied will provide a first guiding region. At the second end 508 of the detection cell, the voltage applied will provide a second guiding region. Of course, the provision of these guiding regions is dependent upon having the appropriate spacial separation of the top and bottom portion of the internal surface of the detection cell 501 at these ends 512, 508. These guiding regions will maintain excitation light 515 from wandering between the first end 512 and the second end 508.

Preferably, the detection cell 501 is also made of a material having an index of refraction less than the support matrix 502, or, alternatively, the top and bottom portions of the internal surface (not shown) are coated with such a material, so that excitation light 515 is also prevented from wandering in a direction normal to the plane in which the first end 512 and the second end 508 reside.

It should be appreciated that the detection cell of the present invention may be utilized with numerous other systems. For example, systems described in U.S. Pat. Nos. 5,584,982; 5,268,080; and 4,675,095, incorporated herein by reference, make incorporate the detection cell of the present invention. One of skill in the art will appreciate other applications for the detection cell of the present invention.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are, therefore, to be considered in all respects as illustrative and not restrictive, the scope of the invention being indicated by the appended claims, and not limited to the foregoing description. In addition, all publications and patents cited herein are incorporated by reference.

What is claimed is:

1. A detection cell, comprising:
    a body comprising a first end that has a first opening, a second end that has a second opening, an interior cavity that fluidly connects said first opening an said second opening, two side portions, a top portion, and a bottom portion wherein at least one of said portions has a substantially flat surface adapted to receive excitation light;
    wherein said interior cavity is adapted to holding a support matrix for receiving a chemical species through said first opening, passing said chemical species through said interior cavity, and discharging said chemical species through said second opening, wherein said receiving and discharging said chemical species defines a direction of flow;
    wherein said excitation light has an axis of travel substantially perpendicular to said direction of flow; and
    wherein at least two of said first end, second end, each of said side portions, said top portion and said bottom portions are adapted to providing a first and a second guiding region, respectively, each having an index of refraction less than that of said support matrix.

2. The detection cell of claim 1, whereupon the application of an electric field across said support matrix creates said first and second guiding regions at said first end and said second end, respectively.

3. The detection cell of claim 2, wherein said top portion comprises a top internal surface and said bottom portion comprises a bottom internal surface disposed opposite each other such that each internal surface extends from said first end to said second end, wherein said top and bottom internal surfaces are disposed closest to each other at said first and second ends.

4. The detection cell of claim 3, wherein said top and bottom internal surfaces are disposed approximately 100 $\mu$m apart from each other at said first and second ends.

5. The detection cell of claim 3, wherein said top and bottom internal surfaces each comprise a substantially symmetrical curve.

6. The detection cell of claim 3, wherein said top and bottom internal surfaces each comprise a substantially symmetrical curve that are substantially symmetrical relative to each other.

7. The detection cell of claim 6, wherein said substantially symmetrical curves are concave.

8. The detection cell of claim 1, wherein said top portion comprises a top internal surface and said bottom potion comprises a bottom internal surface disposed opposite each other, wherein each internal surface have an index of refraction less than that of said support matrix, thereby providing said first and second guiding regions, respectively.

9. The detection cell of claim 8, wherein said top and bottom portions comprise amorphous fluoropolymer.

10. The detection cell of claim 8, wherein said top portion comprises a first coating and said bottom portion comprises a second coating, wherein each coating has an index of refraction less than that of said support matrix.

11. The detection cell of claim 10, wherein said first and second coatings comprise amorphous fluoropolymer.

12. The detection cell of claim 11, wherein said cell is fused silica.

13. The detection cell of claim 8, wherein said indices of refraction of said top and bottom portions are each lass than approximately 1.45.

14. The detection cell of claim 13, wherein said indices of refraction of said top and bottom portions are each less than approximately 1.33.

15. The detection cell of claim 14, wherein said indices of refraction of said top and bottom portions are each approximately 1.29 to 1.31.

16. The detection cell of claim 8, wherein said top and bottom portions are approximately 100 $\mu$m apart from each other.

17. The detection cell of claim 1, whereupon the application of an electric field across said support matrix creates said first and second guiding regions at said first end and said second end respectively, and wherein said top portion comprises a top internal surface and said bottom portion comprises a bottom internal surface disposed opposite each other, wherein each internal surface have an index of refraction less than that of said support matrix, thereby providing a third and fourth guiding region, respectively.

18. The detection cell of claim 17, wherein said top and bottom internal surfaces are disposed approximately 100 $\mu$m apart from each other at said first and second ends.

19. The detection cell of claim 17, wherein said top and bottom internal surfaces each comprise a substantially symmetrical curve that are substantially symmetrical relative to each other.

20. The detection cell of claim 17, wherein said indices of refraction of said top and bottom internal surfaces are each less than approximately 1.45.

21. The detection cell of claim 17, wherein said indices of refraction of said top and bottom internal surfaces are each less than approximately 1.33.

22. The detection cell of claim 17, wherein said indices of refraction of said top and bottom internal surfaces are each less than approximately 1.29 to 1.31.

23. The detection cell of claim 1, wherein said first opening is configured to receive said chemical species from any of a plurality of capillary tubes.

24. The detection cell of claim 1, wherein said first opening is configured to receive said chemical species from any of a plurality of channels on a microchip.

25. A detection cell, comprising:
a body comprising a first end that has a first opening, a second end that has a second opening, an internal surface that defines an interior cavity that fluidly connects said first opening and said second opening, wherein said interior cavity adapted to hold a support matrix, and an external surface comprising a substantially flat portion adapted to receive excitation light;
wherein said body is adapted to provide a first and second guiding region, each guiding region, having an index of refraction less than that of said support matrix;
wherein a chemical species defines a direction of flow from said first opening to said second opening; and
wherein said excitation light has an axis of travel substantially perpendicular to said direction of flow.

26. The detection cell of claim 25, wherein said first and second guiding regions comprise said first opening and said second opening, respectively, whereupon the application of an electric current across said support matrix creates said first and second guiding regions at said first end and said second end, respectively.

27. The detection cell of claim 26, wherein said internal surface comprises a top internal surface and a bottom internal surface disposed opposite each other, wherein each internal surface extends from said first end and said second end, and wherein said top and bottom internal surfaces are disposed closest to each other at said first and second ends.

28. The detection cell of claim 27, wherein said top and bottom internal surfaces are disposed approximately 100 $\mu$m apart from each other.

29. The detection cell of claim 27, wherein said top and bottom internal surfaces each comprise a substantially symmetrical curve.

30. The detection cell of claim 27, wherein said top and bottom internal surfaces each comprise a substantially symmetrical curve that are substantially symmetrical relative to each other.

31. The detection cell of claim 30, wherein said substantially symmetrical curves are concave.

32. The detection cell of claim 25, wherein said internal surface comprises a top internal surface and a bottom internal surface opposite each other, wherein each have an index of refraction less than that of said support matrix, there providing said first and second guiding regions, respectively.

33. The detection cell of claim 32, wherein said top and bottom internal surfaces comprise amorphous fluoropolymer.

34. The detection cell of claim 32, wherein said top internal surface comprises a first coating and said bottom internal surface comprises a second coating, wherein each coating has an index of refraction less than that of said support matrix.

35. The detection cell of claim 34, wherein said first and second coatings comprise amorphous fluoropolymer.

36. The detection cell of claim 35, wherein said cell is fused silica.

37. The detection cell of claim 32, wherein said indices of refraction of said top and bottom internal surfaces are each less than approximately 1.45.

38. The detection cell of claim 37, wherein said indices of refraction of said top and bottom internal surfaces are each less than approximately 1.33.

39. The detection cell of claim 38, wherein said indices of refraction of said top and bottom internal surfaces are each approximately 1.29 to 1.31.

40. The detection cell of claim 32, wherein said top and bottom internal surfaces are approximately 100 $\mu$m apart from each other.

41. A detection cell, comprising:
a body comprising a first end that has a first opening, a second end that has a second opening, an interior cavity that fluidly connects said first opening and said second opening, wherein said interior cavity is adapted to hold a support matrix, two side portions, a top portion, and a bottom portion, wherein at least one of said portions has a substantially flat surface adapted to receive excitation light;
wherein at least four of said first end, said second end, each of said side portions, said top portion, and said bottom portion are adapted to providing a first, a second, a third, and a fourth guiding region, respectively, each having an index of refraction less than that of said support matrix;

wherein a chemical species defines a direction of flow from said first opening to said second opening; and wherein said excitation light has an axis of travel substantially perpendicular to said direction of flow.

42. The detection cell of claim 41, wherein at least two of said four comprise said first opening and said second opening, whereupon the application of an electric field creates at least two of said guiding regions at said first end and said second end, respectively.

43. The detection cell of claim 41, wherein said top portion comprises a top internal surface and said bottom portion comprises a bottom internal surface disposed opposite each other, wherein each have an index of refraction less than that of said support matrix, thereby providing at least two of said four portions, respectively.

44. The detection cell of claim 43, wherein said top and bottom internal surfaces are disposed approximately 100 μm apart from each other at said first and second ends.

45. The detection cell of claim 43, wherein said top and bottom internal surfaces each comprise a substantially symmetrical curve that are substantially symmetrical relative to each other.

46. The detection cell of claim 43, wherein said indices of refraction of said top and bottom internal surfaces are each less than approximately 1.45.

47. The detection cell of claim 43, wherein said indices of refraction of said top and bottom internal surfaces are each less than approximately 1.33.

48. The detection cell of claim 43 wherein said indices of refraction of said top and bottom internal surfaces are each less than approximately 1.29 to 1.31.

* * * * *

UNITED STATES PATENT AND TRADEMARK OFFICE
CERTIFICATE OF CORRECTION

PATENT NO. : 6,797,139 B2 Page 1 of 1
DATED : September 28, 2004
INVENTOR(S) : Bahatt et al.

It is certified that error appears in the above-identified patent and that said Letters Patent is hereby corrected as shown below:

<u>Column 14,</u>
Line 23, "opening an said" should read -- opening and said --.
Line 67, "said bottom potion" should read -- said bottom portion --.

<u>Column 15,</u>
Line 16, "each lass than" should read -- each less than --.
Line 30, "second end respectively," should read -- second end, respectively, --.

Signed and Sealed this

Twenty-third Day of May, 2006

JON W. DUDAS
*Director of the United States Patent and Trademark Office*